United States Patent [19]

Trotz et al.

[11] Patent Number: 4,565,856
[45] Date of Patent: Jan. 21, 1986

[54] PYRITHIONE-CONTAINING BIOACTIVE POLYMERS AND THEIR USE IN PAINT AND WOOD PRESERVATIVE PRODUCTS

[75] Inventors: Samuel I. Trotz, Orange; Theodore H. Fedynyshyn, Branford, both of Conn.

[73] Assignee: Olin Corporation, Cheshire, Conn.

[21] Appl. No.: 660,208

[22] Filed: Oct. 12, 1984

[51] Int. Cl.$^4$ ............................................. C08F 26/06
[52] U.S. Cl. .................... 526/265; 527/103; 527/314
[58] Field of Search .............. 523/122; 526/265; 527/103, 314, 315

[56] References Cited

U.S. PATENT DOCUMENTS

| | | | |
|---|---|---|---|
| 2,758,116 | 8/1956 | Wiselogle et al. | 260/294.8 |
| 2,809,971 | 10/1957 | Bernstein et al. | 523/122 |
| 3,645,988 | 2/1972 | Hammer et al. | 260/80.72 |
| 3,723,435 | 3/1973 | Furia et al. | 523/122 |
| 3,725,327 | 4/1973 | Stearns et al. | 523/122 |
| 4,191,579 | 3/1980 | Hails et al. | 106/15 R |

FOREIGN PATENT DOCUMENTS

| | | | |
|---|---|---|---|
| 3328095 | 2/1984 | Fed. Rep. of Germany | 523/122 |
| 53-12403 | 2/1978 | Japan . | |
| 54-78733 | 6/1979 | Japan . | |
| 55-36221 | 3/1980 | Japan | 523/122 |

OTHER PUBLICATIONS

J. Polym. Sci. Polymer Letters Edition No. 8, vol. 15, pp. 487–491 (1977), Aug.

Charles U. Pittman, Jr. & Kevin Lawyer, Abstract of Paper "Polymer Bound Fungicides for Paints, Synthesis Testing", presented at American Chemical Society Meeting, Mar. 29–Apr. 3, 1981.

G. Allan Stall and Charles U. Pittman, Jr., "Polymer Films Containing Chemical Bound Fungicides, An Introduction", Journal of Coatings Technology, vol. 50, No. 639, Apr. 1978, pp. 62–65.

*Primary Examiner*—Paul R. Michl
*Assistant Examiner*—N. Sarofim
*Attorney, Agent, or Firm*—William A. Simons; Thomas P. O'Day

[57] ABSTRACT

Disclosed is a bioactive polymer comprising an effective biocidal amount of moieties derived from pyrithione and having the formula

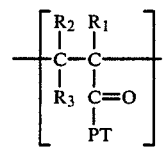

wherein $R_1$, $R_2$ and $R_3$ are individually selected from hydrogen and alkyl groups having from 1 to 4 carbon atoms; and PT represents the pyrithione moiety which is defined as

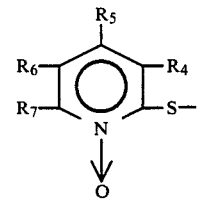

wherein $R_4$, $R_5$, $R_6$ and $R_7$ are individually selected from hydrogen and, a lower alkyl group having from 1 to about 8 carbon atoms, a lower alkoxy group having from 1 to about 8 carbon atoms, a nitro group and a halo group.

8 Claims, No Drawings

PYRITHIONE-CONTAINING BIOACTIVE POLYMERS AND THEIR USE IN PAINT AND WOOD PRESERVATIVE PRODUCTS

BACKGROUND OF THE INVENTION

1. Field of the Invention

This invention relates to pyrithione-containing polymers. This invention also relates to the use of these polymers as biocides in paints and wood preservative products.

2. Brief Description of the Prior Art

Biocides are required in many paint and wood preservative formulations to prevent microbial degradation during shipment, storage or use. Biocides are also required in these formulated products to help protect the coated substrate from harmful microorganisms such as bacteria and fungi and the like.

Biocides used in paint products may be grouped into three major classes: preservatives, mildewcides and antifoulants. Preservatives are widely used in water-based paint systems to prevent in-can bacterial and fungal degradation during storage and shipment. They are particuarly useful in latex systems such as synthetic rubber, polyacrylate, and natural rubber latexes. Mildewcides are employed to prevent degradation of the dried paint films and underlying substrate by microorganisms. Antifoulant paints are used to prevent the growth of organisms on the hulls of both commercial and pleasure boats. The attachment of such organisms decreases the operating efficiency of the boats and increases their maintenance costs.

Mercurial-type biocides have been widely used as both preservatives and mildewcides in paints. They have excellent performance in both functions in many situations. They offer the fast kill time and can control high levels of bacterial contamination. Unfortunately, they are hazardous to handle and may present environmental problems. Thus, their use may be limited to certain applications. Various nonmercurial preservatives and mildewcides have been increasingly considered as substitutes for mercurial compounds.

A wide variety of biocides have been tried as marine antifoulants, but the marketplace has been dominated by cuprous oxide and organotin compounds for this use. Cuprous oxide has been popular because it is efficient, relatively economical, and is specified in many military antifouling paint formulations as the exclusive biocide. However, this chemical causes microporosity in the paint film, which adversely affects efficiency, and it limits the paint colors to dark reddish browns. The use of organotin compounds has been growing in recent years; however, these compounds are more expensive than cuprous oxide and also more difficult to incorporate into paint formulations. Furthermore, they do not leach out completely during use so that when ships are sandblasted the disposal of the contaminated sand poses difficulties. However, organotins yield uniform, tight films without the microporosity problems associated with cuprous oxide and may be formulated in a wide variety of bright or light colors. For these latter reasons, they are widely used on pleasure boats. Since both cuprous oxide and organotin compounds present technical or environmental problems, there is a need for new and better antifoulant paint biocides.

Biocides are also employed as wood preservative products in order to prevent the rapid deterioration of wood products that are exposed to conditions which promote microbial growth and decay. For example, utility poles, cross ties, piling timbers, freshly milled lumber and fence posts as well as wood chip piles used in pulp manufacture require the incorporation of biocides to stop or control fungal attachment. In the past, two classes of biocides have been employed as wood preservatives. One class is oil-borne preservatives (e.g. creosote and pentachlorophenol) while the second class is water-borne salts (e.g. mixtures of inorganic compounds such as copper, chromium, arsenic and zinc salts). The oil-borne preservatives have been the most widely used biocides for wood preservation. However, products treated with these mixtures may have messy oily surfaces. Also both creosote and pentachlorophenol have been objected to as being environmentally hazardous. The water-borne salts are also toxic chemicals which are dissolved in water and injected into wood products where they become bound to or within the wood. These salts have certain advantages over the oil-borne treatments. They leave a cleaner surface that may be more readily painted. Also, their water soluble characteristics provide savings in solvent costs. However, the use of chromium and arsenic salts also present environmental problems.

Because all of these commercially used wood preservatives present these problems, there is a need for new and better wood preservative biocides.

Separately, zinc and sodium pyrithione (also known as the zinc complex and the sodium salt of 1-hydroxy-2-pyridinethione, respectively) are well-known biocides in the cosmetic and hair shampoo fields. However, merely blending these biocides into paint and wood preservative formulations may result in one or more problems. Some of the major problems concern their insolubility in the other constituents of the system and their water solubility. Their paint and wood-preservative constituent insolubility may cause agglomerization of the biocide in the dried film. Their water solubility may cause leaching from the paint film or migration of the biocide in the film. These lead to uneven biocidal protection, environmental problems and reduced service life.

It has been found that these paint or wood preservative constituent insolubility and water solubility problems may be corrected by immobilizing the pyrithione moiety in selected polymers. This attachment of this moiety to these selected polymers results in the formation of a bioactive polymer.

Accordingly, it is an object of this invention to provide a class of bioactive polymers which are effective as preservatives, mildewcides and marine antifoulants in paints as well as wood preservatives.

It is also an object of this invention to provide a class of bioactive polymers which do not have the undesirable characteristics of many present commercial products such as leaching of the bioactive agent, yet, are highly toxic to the organisms of concern but have low toxicity to humans and wildlife as well as be cost competitive.

Still further objects and advantages of the present invention will be apparent from the following description.

BRIEF SUMMARY OF THE INVENTION

The present invention, therefore, is directed to bioactive polymers comprising an effective biocidal amount of moieties derived from pyrithione and having the formula (I):

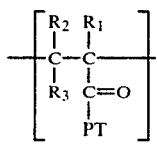

wherein $R_1$, $R_2$ and $R_3$ are individually selected from hydrogen and alkyl groups having from 1 to 4 carbon atoms; and PT represents the pyrithione moiety which is defined by the following formula (II) wherein the pyrithione moiety is connected through the sulfur atom:

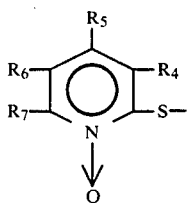

wherein $R_4$, $R_5$, $R_6$ and $R_7$ are individually selected from hydrogen, lower alkyl group having 1 to about 8 carbon atoms, lower alkoxy group having 1 to about 8 carbon atoms, a nitro group and a halo group (e.g. F, Cl, Br and I).

These moieties of formula (I) may be made into homopolymers or incorporated into copolymers, terpolymers and the like containing moieties of at least one ethylenically unsaturated comonomer. Such polymers may have average molecular weights from about 1000 to about 1,000,000.

The present invention is also directed toward the use of these bioactive polymers as paint preservatives, mildewcides in paints, antifoulant agents in paints and as wood preservative biocides as described below.

DETAILED DESCRIPTION

The monomeric moieties of formula (I) may be made by reacting sodium pyrithione with a corresponding vinyl-containing acid chloride compound. This reaction may be carried out in the presence of water or suitable organic solvent. This reaction is illustrated by the following reaction (A) where sodium pyrithione is reacted with methacryloyl chloride:

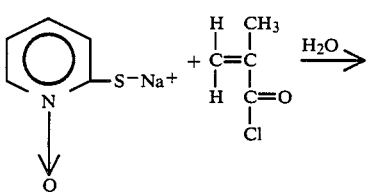

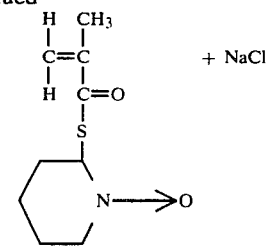

Suitable vinyl-containing acid chloride reactants include methacryloyl chloride, 3,3-dimethylacryloyl chloride and crotyl chloride. The most preferred is methacryloyl chloride ($R_1 = CH_3$, $R_2 = R_3 = H$) because of cost considerations and its good compatability in paint formulations, especially methacrylate-based.

The preferred pyrithione moiety is the unsubstituted pyrithione ($R_4 = R_5 = R_6 = R_7 = H$). It is widely available as sodium pyrithione.

The reaction between these vinyl acid chlorides and sodium pyrithione may be carried out with any conventional reaction conditions for this type of condensation reaction. It is preferred to employ a molar excess of the vinyl acid chloride. It is also preferred to employ water as a solvent and at temperatures from about $-10°$ C. to about $+30°$ C. and at atmospheric pressure. Suitable reaction times will range from about 1 to about 5 hours. The formed product will precipitate from the reaction mixture and may be recovered by any conventional solids/liquid separation technique. It is preferred to purify the precipitated product by extraction with a dilute NaOH solution. The recovered product is preferably stored at temperatures below room temperatures (e.g. $-10°$ C. to $+10°$ C.) to prevent decomposition. It should be noted that the reaction parameters for making the moieties of formula (I) are not critical limitations to the present invention and the present invention contemplates any and all suitable reaction conditions.

The pyrithione-containing compounds as described above may be polymerized by any of the conventionally known methods for polymerizing vinyl bond-containing monomers. These may include solvent, bulk, suspension or emulsion-type methods. Various polymerization initiators such as benzoyl peroxide, acetyl peroxide, azobis(isobutyronitrile) (also known as AIBN) or lauryl peroxide may be used. Specifically, the homopolymers and copolymers of this invention may be prepared by any of the procedures conventionally employed for making acrylate or methacrylate homopolymers or copolymers containing said monomers. It is preferred and desirable to conduct the polymerization under an inert gaseous atmosphere (e.g. nitrogen) and in an aqueous solution whereby the monomer or comonomers are suspended. However, it may be desirable in some instances to carry out the polymerization in an organic solvent such as benzene, toluene, hexane, cyclohexane, tetrahydrofuran or the like. Preferably, the monomers and solvent are agitated and the initiator is then added.

The conditions of the reaction, such as the concentrations of the monomer and the initiator, the type of initiator, and of the solvent, vary according to the desired polymer to be formed.

The duration and temperature of the reaction depends on the desired copolymer as well as the solvent and the initiator. Preferably, reaction temperatures from about 40° C. to 100° C. are employed.

At the end of the reactions, the homopolymers or copolymers are separated from the reaction mixture and dried according to conventional techniques.

Suitable ethylenically unsaturated comonomers include the following: ethylene, propylene, butadiene, isoprene, tetrafluoroethylene, vinyl chloride, vinylidine chloride, vinylidine fluoride, styrene, indene, coumarone, vinyl acetate, vinyl alcohol, vinyl formal, acrolein, methyl vinyl ketone, vinyl pyrrolidone, maleic anhydride, acrylonitrile, vinyl ethers having the formula $CH_2=CHOR_8$, acrylic acid, acrylamide, methacrylic esters of the formula $CH_2=C(CH_3)CO_2R_8$, acrylic esters of the formula $CH_2=CHCO_2R_8$ and cyanoacrylic esters having the formula $CH_2=C(CN)CO_2R_8$, wherein $R_8$ is a lower alkyl group having 1 to 4 carbon atoms.

Preferred copolymers of the present invention contain polymeric units or moieties of formula (I), above, as well as polymeric units or moieties derived from other methacrylates or acrylates as disclosed in preceding paragraph. In the case of copolymers, terpolymers and the like, the weight fraction of the monomers of formula (I) may be any amount which results in an effective bioactive polymer. Preferably, this weight fraction may be from about 0.01% to about 50% by weight of the total polymer.

In an alternative embodiment, it is also possible to attach the pyrithione derived moiety of formula (I) to a preformed polymer. For example, a poly(methylacrylate) could be reacted with pyrithione to add this pyrithione moiety at certain sites on the polymer chain.

It is also possible to attach other biocides (e.g. alkyl tin and quaternary ammonium moieties) to the polymer chain besides the pyrithione moiety for a more comprehensive attack on invading organisms.

The bioactive polymers of the present invention have many desirable attributes. They possess good antimicrobial activity and are not incompatible with components of conventional paint and wood preservative products. These polymers are also non-volatile, hydrolytically stable, thermally stable, and may be soluble in water and organic solvents. Furthermore, they form no undesirable colors in the paint and wood preservative formulations or in the resulting dried films. Still further, they are cost competitive with known biocides used in various paints and wood preservative products while having low or no toxicity toward humans and wildlife.

In accordance with one aspect of this invention, it has been found that the polymers containing the moiety of formula (I), above, either as homopolymers or as copolymers, terpolymers, or the like with the ethylenically unsaturated comonomers described above, may be utilized as effective paint preservatives. In practicing this aspect of the invention, an effective paint-preserving amount of one or more of these polymers is incorporated into a paint formulation. It is to be understood that the term "effective paint-preserving amount" as used in this specification and claims is intended to include any amount which will prevent or control degradation of the paint. In-can degradation of paints is often caused by gram-positive bacteria such as *Bacillus cereus* and *Staphylococcus aureus* or gram-negative bacteria such as those of the Pseudomonas or Xanthomonas classes. This degradation of the paint ingredients results in viscosity loss or generation of offensive odors.

Generally, paint preservatives are employed in aqueous-based paint systems such as latex systems. Solvent-based paints usually do not require a preservative since the nonaqueous formulation will not support bacterial growth. In-can preservatives are bactericidal and their killing action must be rapid to prevent bacterial production of certain enzymes which are actually the cause of the latex paint destruction.

When the present bioactive polymers are employed as paint preservatives, it is usually desirable to add them to the paint formulation in the same manner as other polymers are incorporated. For example, it is preferred to incorporate them as a substitute for all or a portion of non-bioactive polymers. As stated above, the actual amount of preservative used will vary with many parameters. Generally, it is preferred to employ from about 0.1 to about 5.0 pounds of the active moiety shown in formula (I) per 100 gallons of total paint formulation for this purpose.

In accordance with another aspect of this invention, it has been found that the polymers containing the moiety of formula (I), above, either as homopolymers or as copolymers, terpolymers or the like made with the ethylenically unsaturated comonomers described above, may be also employed as effective mildewcides. In practicing this aspect of the invention, an effective mildewcidal amount of one or more of these polymers is incorporated into a paint or wood preservative formulation. It is understood that the term "effective mildewcidal amount" as used in this specification and claims is intended to include any amount which will kill or control mildew-causing microorganisms. Mildew or mold causing microorganisms vary according to the exposure environment. *Aureobasidium pullulans* is the most commonly found species in temperate and cooler climates. Tropical and subtropical conditions favor the growth of microogranisms of the classes Aureobasidium, Aspergillus and Pencillium as well as the algae *Pleurococcus virides*. This effective mildewcidal amount will, of course, vary because of changes in the parameters of the environment and the substrate having these polymers incorporated therein. Generally, it is preferred to employ from about 0.1 to about 5.0 pounds of the active moiety shown in formula (I) per 100 gallons of total paint formulation for this purpose.

Paint products which may contain the biocidal compositions of the invention as preservatives and mildewcides include architectural coatings for new and existing structures such as latex and solvent interior and exterior paints. Other suitable paint products would include industrial finishing products such as interior and exterior maintainence coatings.

In accordance with still another aspect of the present invention, it has been found that the polymers containing the moiety of formula (I), above, either as homopolymers or as copolymers, terpolymers or the like with the ethylenically unsaturated comonomers described above, may be utilized as effective antifoulant materials. In practicing this aspect of the invention, an effective antifoulant amount of one or more of these polymers is incorporated into a hull coating formulation. It is understood that the term "effective antifouling amount" as used in this specification and claims is intended to include any amount which will prevent or control fouling on the hull. Fouling organisms include plant forms such as algae and animal forms such as those of the classes Anthropeda, Coelenterata and Mollusca. The green algae Enteromorpha is the organism most often found on the hulls of large ships.

This effective antifouling amount will vary because of changes in the parameters of the environments and the substrate in which it is applied to the hulls. Generally, it is preferred to employ from about 1 to about 50 pounds of the active moiety shown in formula (I) per 100 gallons of total paint formulation for this purpose.

In accordance with still another aspect of this invention, it has been found that polymers containing the moiety of formula (I), above, either as homopolymers or as copolymers, terpolymers and the like with the ethylenically unsaturated comonomers described above, may be utilized as effective wood preservatives. In practicing this aspect of the present invention, an effective wood-preserving amount of one or more of these polymers is incorporated into a wood product. It is to be understood that the term "effective wood-preserving amount" as used in this specification and claims is intended to include any amount which will prevent or control degradation of the wood product. Wood products not in water are subject to two forms of fungal attack, surface attack (e.g. soft rot) and internal attack (e.g. white and brown rots). Fungi imperfecti and Ascomycetes are the major cause of soft rot and the Basidiomycetes class of fungi is the major cause of internal attack. White rots attack the lignin and brown rots attack the cellulose. The commonly known dry rot is a brown rot. Also, wood products exposed to seawater may be attacked by marine organisms such as Pholads, Teredo, and *Limnoria tripunctata*. The effective amount of polymer employed in this application may be constantly changing because of the possible variation of many parameters. Some of these parameters may include the specific preserving polymers employed, the type of wood product to be protected, and the type of environment the wood product is exposed to. Generally, it is preferred to employ from about 1 to about 50 pounds of the active moiety shown in formula (I) per 100 gallons of total wood preservative formulation.

The biocides of the present invention may be added to the wood products by either pressure or nonpressure impregnation. If pressure impregnation is employed, either air, hydrostatic pressure and vacuum methods, or combinations thereof, may be used. If nonpressure impregnation of wood is desired, either dipping, spraying, brushing or the like may be desirable.

These bioactive polymers of the present invention may be either added directly to cellulosic materials such as the wood products in a preformed state, or the monomeric precursors including those of formula (I) may be added with suitable catalyst to promote the polymerization in-situ. In this latter case, these bioactive polymers may or may not be chemically bonded to the polysaccharide structure of the cellulosic material (e.g. wood, paper and the like). It should also be noted that paper products may be treated in either fashion to make a mildew-resistant paper, cardboard boxes or the like.

The invention is further illustrated by the following examples and comparison examples. All parts and percentages are by weight unless explicitly stated otherwise.

SYNTHESIS EXAMPLES

EXAMPLE 1

Synthesis of Pyrithione Methacrylate Homopolymer

Part A—Production of Pyrithione Methacrylate Monomer

A 2-liter beaker was charged with 158.8 g of 40% aqueous sodium pyrithione (0.5 mole) and 200 ml of water. A dropping funnel was charged with 90.4 ml of methacryloyl chloride (0.75 mole). The 2-liter beaker was cooled to +5° C. with an ice/water bath. The acid chloride was added dropwise over 90 minutes. During addition the temperature of the solution was maintained between +5° C. and +9° C. After addition was completed the solution was stirred at +6° to +7° C. for 1 hour. A solution of 20 g sodium hydroxide (0.5 mole) in 300 ml of water was added over 10 minutes. After stirring an additional 15 minutes at +8° to +10° C. the solution was brought to room temperature and stirred for 1 hour. The yellow solid that had formed was filtered and then washed with 200 ml of water. The solid was dissolved in 800 ml of methylene chloride and extracted three times with 500 ml of 4% sodium hydroxide. The methylene chloride solution was dried over 60 g of magnesium sulfate for 15 minutes, filtered, and concentrated via roto-evaporation, to give 69.18 g of a yellow solid for a 66.7% yield, with an assay of 94.1%.

The structure was confirmed by $^1$H-NMR, $^{13}$C-NMR and IR.

Purification via preparative liquid chromotography gave an analytical sample having a m.p. of 146°–147° C.

Elemental Analysis: for $C_9H_9NSO_2$: Theory: C, 55.37; H, 4.65; N, 7.17; S, 16.42: Found: C, 56.08; H, 4.80; N, 6.52; S, 14.87.

Part B—Production of Pyrithione Methacrylate Homopolymer

A 6-ml flask was charged with 0.975 g of pyrithione methacrylate (5 mmole), 0.083 g of azobis(isobutyronitrile) (AIBN) (0.5 mmole), and 4 ml of toluene. The flask was sealed and placed in an oven at 80° C. for 16 hours. After cooling to room temperature the product was diluted with 10 ml of methylene chloride and filtered. The solution was , concentrated via roto-evaporation and 1.00 g of the desired product was isolated as a brown oil in quantitative yield. The structure was confirmed by NMR and IR. Similar results were obtained by employing either acetyl peroxide, benzoyl peroxide or lauryl peroxide as the radical initiator.

EXAMPLE 2

Synthesis of 1:9 Pyrithione Methacrylate/Methyl Methacrylate Co-Polymer by the Solution Copolymerization Method A 6-ml flask was charged with 0.487 g of pyrithione methacrylate (2.5 mmole), 2.40 ml of methyl methacrylate (22.5 mmole), 0.083 g of AIBN (0.5 mmole), and 3 ml of toluene. The flask was sealed and placed in an oven at 80° C. for 16 hours. After cooling to room temperature the product was diluted with 10 ml of methylene chloride and filtered. The solution was concentrated via roto-evaporation and 2.24 g of the desired product was isolated as a yellow polymeric material for a 79.4% yield. The structure was confirmed by NMR and IR. Similar results were obtained by employing either acetyl peroxide, benzoyl peroxide, or lauryl peroxide as the radical initiator.

EXAMPLE 3

Synthesis of 1:9 Pyrithione Methacrylate/Methyl Methacrylate Copolymer by Bulk Copolymerization A 6-ml flask was charged with 0.487 g of pyrithione methacrylate (2.5 mmole), 2.40 ml of methyl methacrylate (22.5 mmole) and a 0.083 g of AIBN (0.5 mmole). The flask was sealed and placed in an oven at 80° C. for 16 hours. After cooling to room temperature, the product was diluted with 15 ml of methylene chloride and filtered. The solution was concentrated via roto-evaporation and 2.41 g of the desired product was isolated as a yellow polymeric material for a 85.7% yield. The structure was confirmed by NMR and IR. Similar results were obtained by employing either acetyl peroxide, benzoyl peroxide, or lauryl peroxide as the radical initiator.

EXAMPLE 4

Synthesis of 1:49 Pyrithione Methacrylate/Methyl Methacrylate Copolymer by Solution Copolymerization A 6-ml flask was charged with 0.097 g of pyrithione methacrylate (0.5 mmole), 2.60 ml of methyl methacrylate (24.5 mmole), 0.083 g of AIBN (0.5 mmole), and 3 ml of toluene. The flask was sealed and placed in an oven at 80° C. for 16 hours. After cooling to room temperature, the product was diluted with 10 ml of methylene chloride and filtered. The solution was concentrated via roto-evaporation, and 2.30 g of the desired product was isolated as a white polymeric material for a 90.2% yield. The structure was confirmed by NMR and IR. Similar results were obtained by employing either acetyl peroxide, benzoyl peroxide, or lauryl peroxide as the radical initiator.

EXAMPLE 5

Synthesis of 1:49 Pyrithione Methacrylate/Methyl Methacrylate Copolymer by Bulk Copolymerization A 6-ml flask was charged with 0.097 g of pyrithione methacrylate (0.5 mmole), 2.60 ml of methyl methacrylate (24.5 mmole) and 0.083 g of AIBN (0.5 mmole). The flask was sealed and placed in an oven at 80° C. for 16 hours. After cooling to room temperature, the product was diluted with 15 ml of methylene chloride and filtered. The solution was concentrated via roto-evaporation and 2.18 g of the desired product was isolated as a white polymeric material for an 85.5% yield. The structure was confirmed by NMR and IR. Similar results were obtained by employing either acetyl peroxide, benzoyl peroxide, or lauryl peroxide as the radical initiator.

EXAMPLE 6

Synthesis of 1:9 Pyrithione Methacrylate/Styrene Copolymer by Solution Copolymerization A 6-ml flask was charged with 0.489 g of pyrithione methacrylate (2.5 mmole), 2.6 ml of methyl methacrylate (22.5 mmole) and 0.083 g of AIBN (0.5 mmole), and 3 ml of toluene. The flask was sealed and placed in an oven at 80° C. for 16 hours. After cooling to room temperature, the product was diluted with 10 ml of methylene chloride and filtered. The solution was concentrated via roto-evaporation and 2.32 g of the desired product was isolated as a yellow polymeric material for a 79.6% yield. The structure was confirmed by NMR and IR. Similar results were obtained by employing either acetyl peroxide, benzoyl peroxide, or lauryl peroxide as the radical initiator.

EXAMPLE 7

Synthesis of 1:9 Pyrithione Methacrylate/Styrene Copolymer by Bulk Copolymerization A 6-ml flask was charged with 0.489 g of pyrithione methacrylate (2.5 mmole), 2.6 ml of styrene (22.5 mmole) and 0.083 g of AIBN (0.5 mmole). The flask was sealed and placed in an oven at 80° C. for 16 hours. After cooling to room temperature, the product was diluted with 10 ml of methylene chloride and filtered. The solution was concentrated via roto-evaporation and 1.66 g of the desired product was isolated as a yellow polymeric material for a 56.9% yield. The structure was confirmed by NMR and IR. Similar results were obtained by employing either acetyl peroxide, benzoyl peroxide, or lauryl peroxide as the radical initiator.

EXAMPLE 8

Synthesis of 1:24 Pyrithione Methacrylate/Methyl Methacrylate Copolymer by Solution Polymerization The procedure in Example 4 was repeated to make a 1:24 pyrithione methacrylate/methyl methacrylate copolymer as a white polymer solid in 71.9% yield.

EXAMPLE 9

Synthesis of 1:99 Pyrithione Methacrylate/Methyl Methacrylate Copolymer by Solution Polymerization The procedure in Example 4 was repeated to make a 1:99 pyrithione methacrylate/methyl methacrylate copolymer as a white polymeric solid in 52.3% yield.

EXAMPLE 10

Synthesis of 1:19 Pyrithione Methacrylate/Methyl Methacrylate Copolymer by Solution Polymerization The procedure in Example 4 was repeated to make a 1:19 pyrithione methacrylate/methyl methacrylate copolymer as a white solid in 78.8% yield.

EXAMPLE 11

Synthesis and Purification of 1:4.4 Pyrithione Methacrylate/Methyl Methacrylate Copolymer A 150-ml flask was charged with 60.6 g of methyl methacrylate (0.6 mole), 26.4 g of pyrithione methacrylate (0.135 mole), 3.69 g of 70% benzoyl peroxide in water (0.011 mole) and 60 ml of toluene. The flask was sealed and placed in an oven at 85° C. for 16 hours. After cooling to room temperature the product was diluted with 60 ml of methylene chloride and filtered. The solution was concentrated via roto-evaporation and 65.49 g of the desired product was isolated as a yellow polymeric solid for a 73.1% yield.

The crude polymer was twice precipitated from 200 ml of methylene chloride into 2000 ml of mixed hexanes. The light yellow polymer was filtered and dried under vacuum for 1 hour to give 60.32 g of purified polymer in a 69.7% overall yield.

The structure was confirmed by NMR and IR. Analysis showed that the polymer contained 13.69% pyrithione by weight.

EXAMPLE 12

Synthesis and Purification of 1:5 Pyrithione Methacrylate/(4:1) Methyl Methacrylate/Butyl Acrylate Terpolymer By Solution Polymerization A 250-ml flask was charged with 101.0 g of methyl methacrylate (1.0 mole), 24.4 g of pyrithione methacrylate (0.125 mole), 16.1 g of butyl acrylate (0.125 mole), 6.15 g of 70% benzoyl peroxide in water (0.018 mole) and 100 ml of toluene. The flask was sealed and placed in an oven at 85° C. for 16 hours. After cooling to room temperature the product was diluted with 100 ml of methylene chloride and filtered. The solution was concentrated via roto-evaporation and 109.19 g of the desired product was isolated as a pale yellow polymeric solid for a 74.9% yield.

The polymer was purified according to the method of Example 11 to give 106.82 g of a pale yellow solid in a 73.7% overall yield.

The structure was confirmed by NMR and IR. Analysis showed that the polymer contained 7.30% pyrithione by weight.

EXAMPLE 13

Synthesis and Purification of 1:9 Pyrithione Methacrylate/(16:84) Methyl Methacrylate-Butyl Acrylate Terpolymer A 150-ml flask was charged with 60.06 g of methyl methacrylate (0.6 mole), 7.32 g of pyrithione methacrylate (0.0375 mole), 14.49 g of butyl acrylate (0.1125 mole), 3.69 g of 70% benzoyl peroxide in water (0.011 mole) and 60 ml of toluene. The flask was sealed and placed in an oven at 85° C. for 16 hours. After cooling to room temperature the product was diluted with 60 ml of methylene chloride and filtered. The solution was concentrated via roto-evaporation and 56.94 g of the desired product was isolated as a pale yellow polymeric solid for a 67.4% yield.

The polymer was purified according to the method of Example 11 to give 54.85 g of a pale yellow solid in a 64.9% overall yield.

The structure was confirmed by NMR and IR. Analysis showed that the polymer contained 4.03% pyrithione by weight.

EXAMPLE 14

Synthesis of 1:49 Pyrithione Methacrylate/Methyl Methacrylate Copolymer by Emulsion Polymerization With a REDOX Initiator The reaction was performed under a nitrogen atmosphere. A 500-ml, 3-neck flask was charged with 12 g of Triton X-200 surfactant and 188 ml of water. A solution of 3.90 g of pyrithione methacrylate (0.02 mmole) in 104.8 ml of methyl methacrylate (0.98 mole), 0.5 g of ammonium persulfate, and 2 ml of a solution of 0.3 g of ferrous sulfate heptahydrate in 200 ml of water was prepared and added to the 3-neck flask. After stirring for 30 minutes, 0.5 g of sodium metabisulfate and 3 drops of 70% t-butylhydroperoxide was added to the flask. After a 30 minute induction period, the temperature of the reaction quickly rose to 85° C. The emulsion was allowed to slowly cool to room temperature and then it was filtered through a plug of glass wool to give 288 g of a white emulsion. A 25.05-g aliquot was dried at 60° C. overnight to give 8.51 g of a white solid. The emulsion contained 33.9% by weight solids for a yield of 91.7%. The structure was confirmed by NMR and IR.

EXAMPLE 15

Synthesis of 1:19 Pyrithione Methacrylate/(1:1) Methyl Methacrylate-Butyl Acrylate Terpolymer by Emulsion Polymerization An emulsion was prepared by adding in order with vigorous stirring, 50 ml of water, 6 g of Triton X-200 surfactant, 0.2 g of ammonium persulfate, and a solution of 4.88 g of pyrithione methacrylate (0.025 mole), 23.78 g of methyl methacrylate (0.2375 mole) and 30.44 g of butyl acrylate (0.2375 mole). After stirring an additional 10 minutes the emulsion was placed in a dropping funnel. A 300-ml, 3-neck flask was charged with 10 ml of water and 15 ml of the emulsion. The emulsion was heated and polymerization started between 78°–80° C. The contents of the dropping funnel were added over 2 hours with the temperature of the emulsion maintained between 82°–86° C. After addition was completed, the emulsion was heated an additional 1 hour at 90°–92° C. The emulsion was cooled to room temperature and stirred overnight. The emulsion was filtered through a plug of glass wool to give 135.0 g of a white emulsion. A 20.12 g aliquot was heated at 40° C. for 2 days to give 4.01 g of a white solid. The emulsion contained 19.9% by weight solids for a yield of 44.1%. The structure was confirmed by NMR and IR.

EXAMPLE 16

Synthesis of 1:49 Pyrithione Methacrylate/(1:1) Methyl Methacrylate-Butylacrylate Terpolymer by Emulsion Polymerization An emulsion was prepared by adding in order with vigorous stirring, 50 ml of water, 6 g of Triton X-200 surfactant, 0.2 g of ammonium persulfate, and a solution of 1.95 g of pyrithione methacrylate (0.01 mole), 24.53 g of methyl methacrylate (0.245 mole) and 31.42 g of butylacrylate (0.245 mole). After stirring an additional 10 minutes the emulsion was placed in a dropping funnel. A 300-ml, 3-neck flask was charged with 10 ml of water and 15 ml of the emulsion. The emulsion was heated and polymerization started between 78°–80° C. The contents of the dropping funnel were added over 2 hours with the temperature of the emulsion maintained between 83°–86° C. After the addition was completed the emulsion was heated an additional 1 hour at 90°–91° C. The emulsion was allowed to reach room temperature and stirred overnight. The emulsion was filtered through a plug of glass wool and 134.05 g of a white emulsion was isolated. A 20.22-g aliquot was heated at 40° C. for 2 days to give a 7.78 g of a white solid. The emulsion contained 38.5% by weight solids for a yield of 86.3%. The structure was confirmed by NMR and IR analysis.

EXAMPLE 17

Synthesis of 1:49 Pyrithione Methacrylate/(3:2) Methyl Methacrylate-Butyl Acrylate Terpolymer By Emulsion Polymerization The procedure in Example 15 was repeated to make a 1:49 pyrithione methacrylate/(3:2) methyl methacrylate/butyl acrylate terpolymer in 90.0% yield.

EXAMPLE 18

Synthesis of 1:19 Pyrithione Methacrylate/(4:1) Methyl Methacrylate-Butyl Acrylate Terpolymer The procedure in Example 12 was repeated to make a 1:19 pyrithione methacrylate/(4:1) methyl methacrylate/butyl acrylate terpolymer as a white solid in a 67.6% yield. Analysis showed that the polymer contained 3.96% pyrithione by weight.

EXAMPLE 19

Synthesis of 3:17 Pyrithione Methacrylate/Methyl Methacrylate Copolymer

The procedure in Example 12 was repeated to make a 3:17 pyrithione methacrylate/methyl methacrylate copolymer as a pale yellow solid in a 49.7% yield. Analysis showed that the polymer contained 11.97% pyrithione by weight.

TABLE 1

Molecular Weights of Pyrithione Containing Polymers
Weight-average molecular weights were
determined by gel permeation chromatography (HPLC) and
are reported relative to poly methyl methacrylate.

| Example | Weight Average Molecular Weight |
|---------|-------------------------------|
| 1  | 2,000 |
| 2  | 3,000 |
| 3  | 3,000 |
| 4  | 18,000 |
| 5  | 17,000 |
| 6  | 10,000 |
| 7  | 8,000 |
| 8  | 10,000 |
| 9  | 50,000 |
| 10 | 8,000 |
| 11 | 25,000 |
| 12 | 30,000 |
| 13 | 40,000 |
| 14 | 64,000 |
| 15 | 59,000 |
| 16 | 82,000 |
| 17 | 74,000 |
| 18 | 50,000 |
| 19 | 18,000 |

EXAMPLE 20

Hydrolytic Stability of 1:24 Pyrithione Methacrylate/Methyl Methacrylate at pH of 8.5

A 1:24 pyrithione methacrylate/methyl methacrylate copolymer similar to that of Example 8 was employed. A 6-oz., flat-bottom jar with a 60 mm diameter was charged with 0.9 g of the polymer.

Five ml of methylene chloride was added to the jar to dissolve the polymer. As the methylene chloride evaporated off, a uniform polymer film was deposited on the bottom of the jar. Thirty ml of saturated aqueous sodium bicarbonate (ph=8.5) was added and the jar was capped and wrapped in foil to keep out light. Jars were then gently shaken for the desired amount of time. After an appropriate time interval the aqueous solution was filtered and the amount of sodium pyrithione and other pyrithione derivatives present in the aqueous solution was determined.

Samples were analyzed at day 1, 3, 10, 21, 42 and 84.

From day 1 to day 84 no sodium pyrithione or any derivatives of pyrithione were detected. Under the conditions of the test, no detectable hydrolysis of the pyrithione thioester occurred, and therefore there was no migration of pyrithione from the polymer system. The limit of detection of the test was 0.19% of the pyrithione originally present in the polymer.

Selected polymer films from days 1, 3, 10 and 21 were analyzed by a standard minimum inhibitory concentration (MIC) test to determine their antimicrobial activity after exposure to hydrolysis conditions. Results showed that no decrease in antimicrobial activity was observed in any of the samples tested.

EXAMPLE 21

Hydrolytic Stability of 1:19 Pyrithione Methacrylate/(4:1) Methyl Methacrylate-Butyl Acrylate Terpolymer Films at pH of 2.9.

The 1:19 pyrithione methacrylate/(4:1) methyl methacrylate-butyl acrylate terpolymer prepared in Example 18 was tested for hydrolytic stability by the same method as employed in Example 20 except that 0.1N acetic acid was employed as the solvent. The results are summarized in Table 2.

EXAMPLE 22

Hydrolytic Stability of 1:19 Pyrithione Methacrylate/(4:1) Methyl Methacrylate-Butyl Acrylate Terpolymer Films at pH of 10

The 1:19 pyrithione methacrylate/(4:1) methyl methacrylate-butyl acrylate terpolymer prepared in Example 18 was tested for hydrolytic stability by the same method as employed in Example 20 except that a pH 10 buffer (prepared from sodium bicarbonate and sodium hydroxide) was employed as the solvent. The results are summarized in Table 2.

EXAMPLE 23

Hydrolytic Stability of 3:17 Pyrithione Methacrylate/Methyl Methacrylate Copolymer at pH of 2.9

The 3:17 pyrithione methacrylate/methyl methacrylate copolymer prepared in Example 19 was tested for hydrolytic stability by the same method as employed in Example 20 except that the polymer was diluted 1:3 with a 4:1 methyl methacrylate/butyl acrylate copolymer and 0.1N acetic acid was employed as the solvent. The results are summarized in Table 2.

EXAMPLE 24

Hydrolytic Stability of 3:17 Pyrithione Methacrylate/Methyl Methacrylate Copolymer at pH of 10.0

The 3:17 pyrithione methacrylate/methyl methacrylate copolymer prepared in Example 19 was tested for hydrolytic stability by the same method as employed in Example 20 except that the polymer was tested with a 4:1 methyl methacrylate/butyl acrylate copolymer and a pH 10 buffer (prepared from sodium bicarbonate and sodium hydroxide) was employed as the solvent. The results are summarized in Table 2, below.

TABLE 2

HYDROLYTIC STABILITY OF PYRITHIONE METHA-
CRYLATE CONTAINING POLYMERS
Results are reported in the percent of pyrithione
hydrolyzed relative to that originally present in the
polymer.

| Days in Test | pH 2.9 | | pH 10.0 | |
|---|---|---|---|---|
| | Polymer 21 | Polymer 22 | Polymer 23 | Polymer 24 |
| 1  | 0 | 0 | 0 | 0 |
| 7  | 0 | 0 | 0 | 0 |
| 14 | 0.23% | 0 | 0 | 0 |
| 28 | 0.34% | 0.08% | 0 | 0 |
| 56 | 0.68% | 0.34% | 0.08% | 0.08% |

The limit of detection of the test is 0.08% of the pyrithione present in the polymer. The results show that even under conditions of extreme pH values, outside the range that the polymer would expect to encounter under normal environmental condition, only minimal hydrolysis occurs after 8 weeks. Thus, the pyrithione containing polymers have been shown to be stable to hydrolysis under a wide range of pH's.

Fungal and Algal Repellency Test of Polymers

The bioactive copolymers made by Examples 2 and 4 were tested for fungal and algal repellency. Microscope slides were used as the substrates in both cases. One half of each slide was coated on one side with a film of polymer containing the active agent to be tested. The total slide was exposed to the challenge of either fungi or algae with the expectation that the half of the slide containing the active agent would prevent growth of the challenging organism, while the untreated half would not.

In the fungal test, the slide was placed on the surface of an agar plate which had been seeded with fungi. After incubation for about 14 days, the slide was examined for extent of growth or lack thereof on the treated surface of the slide. Since leaching of the active agent would create an undesirable zone-of-inhibition outside the perimeter of the treated surface of the slide, no growth on the treated surface along with a small or no zone of inhibition was the desired result. The results of this fungal repellency test are shown in Table 3, below. The results show that both the pyrithione-containing polymers of Examples 2 and 4 control the growth of *A. niger* as compared to the control (untreated) surface with minimal or no zones of inhibition in the agar. The latter means the polymers did not leach into the agar. In comparison, the poly methyl methacrylate employed as a negative control allowed moderate growth of the fungus on the treated surface.

In the algal test, the slide was immersed in a nutrient broth which had been inoculated with the algae *Pleurochloris pyrenoidosa*. After an incubation for 30 days (under light) and a water rinse, the slide was examined microscopically and the extent of algal attachment was noted. Total lack of attachment on the treated surface was the desired result. Additional information was obtained by comparing the extent of growth of algae throughout the broth. Significant leaching of the active agent from the treated surface would inhibit growth in the broth as well as on the treated surface. The results of the algal repellancy test are shown in Table 4, below. The results show that the two pyrithione-containing polymers of Example 2 and 4 prevent algal attachment to the treated surfaces as compared to control (untreated) surfaces. Poly methyl methacrylate allowed moderate attachment. In all three cases, little or no undesirable leaching occurred into the broth.

TABLE 3

Fungal (*Aspergillus Niger*) Repellancy Test

| Polymer Films | GROWTH[1] Sample Control Surface | GROWTH[1] Sample Treated Surface | ZONE OF INHIBITION[2] On Agar |
|---|---|---|---|
| 1:19 Pyrithione Methacrylate/ Methyl Methacrylate from Example 2 | 2 | 0 | 1 |
| 1:49 Pyrithione Methacrylate/Methyl Methacrylate from Example 4 | 4 | 1 | 0 |
| Poly Methyl Methacrylate | 4 | 2 | 0 |

Key for Growth/zone of inhibition
0 - no growth/zone of inhibition
1 - slight growth/zone of inhibition
2 - moderate growth/zone of inhibition
3 - heavy growth/zone of inhibition
4 - very heavy growth/zone of inhibition
[1]By microscopic examination of the sparse growth over the surface of the coated and uncoated portions of the slides.
[2]Zone-of-Inhibition: determined in the agar by direct observation.

TABLE 4

Algal (*Pleurochloris pyrenoidosa*) Repellency Test

| Sample | Control Surface | Treated | Broth |
|---|---|---|---|
| 1:19 Pyrithione Methacrylate/Methyl Methacrylate from Example 2 | 2 | 0 | 2 |
| 1:49 Pyrithione Methacrylate/Methyl Methacrylate from Example 4 | 4 | 0 | 4 |
| Poly Methyl Methacrylate | 4 | 2 | 4 |

Key:
0 - no attachment/growth in broth
1 - slight attachment/growth in broth
2 - moderate attachment/growth in broth
3 - heavy attachment/growth in broth
4 - very heavy attachment/growth in broth

PAINT APPLICATION EXAMPLES

EXAMPLE 25

Prototype Antifoulant Marine Paints (A-D)

The following antifoulant paint formulation was prepared. All numbers are in percent by weight. The ingredients were added in order with 2-3 minutes of stirring between each addition and 30 minutes of stirring after the paint was formulated. In making paints containing 0.74% and 0.37% pyrithione, an additional 25 parts of methylene chloride was added to obtain solubility of the polymer and this solvent was evaporated off during the final stirring.

| Formulation: (by weight) | |
|---|---|
| 36.7 | xylene |
| 19.0 | pyrithione-containing polymer |
| 32.8 | zinc oxide |
| 10.2 | ferric oxide |
| 0.6 | silica |
| 0.7 | bentonite |
| 100.0 | |

Paint A contains a 1:9 pyrithione methacrylate/methyl methacrylate copolymer (3.7% pyrithione dry weight) made by a method similar to the method described in Example 2.

Paint B contains a 1:49 pyrithione methacrylate/methyl methacrylate copolymer (0.74% pyrithione dry weight) made by a method similar to the method described in Example 4.

Paint C contains a 1:99 pyrithione methacrylate/methyl methacrylate copolymer (0.37% pyrithione dry weight) made by a method similar to the method described in Example 9.

Comparison Paints D-H—Commercial Marine Antifoulant Paints

The following commercial marine antifoulant coatings were tested:

| Paint | Name | Biocide |
|---|---|---|
| D | Tri-Lux Antifouling Paint[1] | Tributyltin Fluoride |
| E | Tri-Lux Antifouling Paint[1] | Bis(Tributyltin Oxide) |
| F | Woolsey Vine Last Antifouling Paint[2] | Cuprous Oxide |
| G | Woolsey Super Vine Last Antifouling Paint[2] | Cuprous Oxide and Tributyltin |

-continued

| Paint | Name | Biocide |
|---|---|---|
| H | Woolsey Antifouling Boot Top Paint[2] | Fluoride Tributyltin Resinate |

[1]International Paint Company, Inc., New York, NY
[2]Woolsey Marine Division of Metropolitan Greetings, Inc., Brooklyn, NY.

These paints were tested for fungal and algal repellency. The results of that testing are given in Tables 5 and 6, below. Those results in Table 5 show that the paints made from pyrithione-containing polymers are effective in controlling the growth of *A. niger* with minimal zones of inhibition. Most commercial marine paints are effective against *A. niger*, but have undesirably relatively large zones of inhibition which indicate excessive leaching of the bioactive agent. The results in Table 6 show that the paints containing pyrithione are effective in containing attachment of algae to the painted (treated) surface and they are equal in performance to commercial paint products containing higher amounts of copper- or tin-containing biocides.

TABLE 5

Fungal Repellency Test
Inhibition of Growth of *Aspergillus niger*
by Paint Films

| Sample | % Biocide by Weight | GROWTH[1] Control Surface | GROWTH[1] Treated Surface | ZONE-OF-INHIBITION[2] In Agar |
|---|---|---|---|---|
| Prototype Paints | | | | |
| A | 3.7 Pyrithione | 2 | 0 | 1 |
| B | 0.74 Pyrithione | 2 | 0 | 1 |
| C | 0.37 Pyrithione | 2 | 0 | 0 |
| Commercial Paints | | | | |
| D | 5.25 Sn | 1 | 0 | 4 |
| E | 6.1 Sn | 4 | 0 | 3 |
| F | 42 Cu | 4 | 4 | 0 |
| G | 33 Cu/0.4 Sn | 4 | 0 | 1 |
| H | 3.2 Sn | 2 | 0 | 3 |

Key for Table 5
0 - No Growth/zone-of-inhibition
1 - Slight Growth/zone-of-inhibition
2 - Moderate Growth/zone-of-inhibition
3 - Heavy Growth/zone-of-inhibition
4 - Very Heavy Growth/zone-of-inhibition
[1]By microscopic examination of the sparse growth over the surface of the coated and uncoated portions of the slides.
[2]Zone-of-Inhibition: determined in the agar by direct observation.

TABLE 6

Algal Repellency Test

| Sample | Biocides by Weight | Control Surface | Treated Surface | Broth |
|---|---|---|---|---|
| Prototype Paints | | | | |
| A | 3.7 Pyrithione | 4 | 0 | 1 |
| C | 0.37 Pyrithione | 4 | 0 | 4 |
| Commercial Paints | | | | |
| D | 5.25 Sn | 2 | 0 | 1 |
| E | 6.1 Sn | 0 | 0 | 4 |
| F | 42 Cu | 2 | 0 | 4 |
| G | 33 Cu/0.4 Sn | 2 | 0 | 2 |
| H | 3.2 Sn | 0 | 0 | 4 |

Key for Table 6
0 - No Attachment/Growth
1 - Slight Attachment/Growth
2 - Moderate Attachment/Growth
3 - Heavy Attachment/Growth
4 - Very Heavy Attachment/Growth

EXAMPLE 26

Prototype Solvent-Based Paints I–M

The following paint formulation was used. Numbers are in percent by weight. The ingredients were added in order with 2–3 minutes of stirring between each addition and 30 minutes of stirring after the paint was formulated. When preparing the paints containing 0.74% and 0.37% pyrithione, an additional 25 parts of methylene chloride was added to obtain solubility of the final stirring.

| Formulation: (percent by weight) | |
|---|---|
| 36.7 | toluene |
| 19.0 | polymer |
| 43.0 | titanium dioxide |
| 0.6 | silica |
| 0.7 | bentonite |
| 100.0 | |

Paint I contains a 1:9 pyrithione methacrylate/methyl methacrylate polymer made by a method similar to the method described in Example 2.

Paint J contains a 1:24 pyrithione methacrylate/methyl methacrylate polymer made by a method similar to the method described in Example 8.

Paint K contains a 1:49 pyrithione methacrylate/methyl methacrylate polymer made by a method similar to the method described in Example 4.

Paint L contains a 1:99 pyrithione methacrylate/methyl methacrylate polymer made by a method similar to the method described in Example 9.

EXAMPLE 27

Prototype Water-Borne Paints (M–P)

The following paint formulation was used. Numbers are in grams. To the latex emulsion was added the surfactant, followed by a mixture of the combined solids added in several aliquots over 2 minutes. After addition the latex was stirred for 30 minutes.

| Formulation: parts (by weight) | |
|---|---|
| 46.0 | polymer emulsion, 20% solids |
| 0.95 | "Triton-X-200" surfactant[3] |
| 2.12 | hydroxyethyl cellulose |
| 28.75 | titanium dioxide |
| 18.77 | talc |

[3]Made by Rohm and Haas of Philadelphia, PA.

Paint M contains 5:47.5:47.5 pyrithione methacrylate/methyl methacrylate/butyl acrylate terpolymer made by a method similar to the method described in Example 15.

Paint N contains 2:49:49 pyrithione methacrylate/methyl methacrylate/butyl acrylate terpolymer made by a method similar to the method described in Example 16.

Paint O contains 2:58.8:39.2 pyrithione methacrylate/methyl methacrylate/butyl acrylate terpolymer made by a method similar to the method described in Example 17.

Comparison Paint P contains 6:4 methyl methacrylate/butyl acrylate copolymer.

Comparison Paints (Q–T)—Commercial Paints

The following commercial paints were purchased for testing.

| Paint | Name | Biocide |
| --- | --- | --- |
| Q | Evans Best Gloss Latex House and Trim[4] | Tetrachloroisophthalonitrile (TCIN) |
| R | Evans Latex Enamel Patio and Deck[4] | NONE |
| S | Sherwin-Williams Wall and Trim Interior Flat Latex[5] | NONE |
| T | Magicolor's Finest Latex Semigloss Interior[6] | NONE |

[4]Evans Products Company, Roanoke, VA.
[5]Sherwin-Williams Company, Cleveland, OH
[6]Magicolor Paint Company, Wheeling, IL.

Paint Mildewcide Tests

The test procedure was followed exactly from the following published procedure:

R. A. Zabel and W. E. Horner, *Journal of Coatings Technology*, 53, 33–37, (1981), except that the organism *Aureobasidium pullulans* M30-4 was used, isolated from mildewed exterior latex paint. Duplicates were run in each case. Two separate tests were run for slightly different time periods. (See Tables 7 and 8).

The results show that pyrithione containing paints are effective in controlling mildew growth on paint surfaces and in all cases exceed the performance of a commercial paint containing TCIN. Control paints not containing a biocide for mildew control are prone to heavy mildew growth within a 30-day period.

TABLE 7

Paint Mildewcide Test/Prototype and Commercial Paints

| Paint | % Biocide (Dry Weight) | Growth on Paint Surface 30 Days | 44 Days |
| --- | --- | --- | --- |
| I | 3.7 Pyrithione | 1,1 | 1,1 |
| J | 1.5 Pyrithione | 1,1 | 1,1 |
| K | 0.74 Pyrithione | 1,1 | 1,1 |
| L | 0.37 Pyrithione | 1,2 | 1,2 |
| M | 0.93 Pyrithione | 1,1 | 1,1 |
| N | 0.37 Pyrithione | 1,2 | 2,4 |
| O | 0.93 Pyrithione | 2,2 | 2,2 |
| S | — | 4,4 | 4,4 |
| T | — | 4,4 | 4,3 |

Key for Table 7
1 - No stain
2 - Lightly stained at bottom or a few light spots
3 - Heavily stained
4 - Uniformly stained

TABLE 8

Paint Mildewcide Test/Prototype and Commercial Paints

| Paint | % Biocide (Dry Weight) | Growth on Paint Surface 28 Days | 42 Days |
| --- | --- | --- | --- |
| J | 1.5 Pyrithione | 1,1 | 1,1 |
| M | 0.93 Pyrithione | 1,1 | 1,1 |
| P | — | 4,4 | 4,4 |
| Q | 0.25 TCIN | 2,3 | 2,3 |
| R | — | 3,4 | 3,4 |
| S | — | 3,4 | 4,- |

Key for Table 8
1 - No stain
2 - Lightly stained at bottom or a few light spots
3 - Heavily stained at bottom
4 - Uniformly stained

EXAMPLE 28

Prototype Solvent-Based Paints (U–Z)

The following paint formulations were prepared. Numbers are in grams. The ingredients were added in order with 2–3 minutes of stirring between each addition and 30 minutes of stirring after each paint was formulated.

| Formulation: | 18.35 toluene |
| --- | --- |
| | 8.5 polymer |
| | 21.5 titanium dioxide |
| | 0.3 silica |
| | 0.35 bentonite |

The polymers employed in the paint formulations were mixtures of a 80:20 methyl methacrylate/butyl acrylate copolymer (MMA/BA) and a pyrithione methacrylate/methyl methacrylate/butyl acrylate terpolymer (PTMA/MMA/BA) containing 7.3% pyrithione by weight*. The ratios of these polymers employed in each paint formulation (U–Z) are shown below.

| | Polymer Ingredients | |
| --- | --- | --- |
| Paint | PT MA/MMA/BA* (Weight) | MMA/BA* (Weight) |
| U | 7.64 | 1.86 |
| V | 2.30 | 6.20 |
| W | 0.77 | 7.73 |
| X | 0.23 | 8.27 |
| Y | 0.08 | 8.42 |
| Z | 0.00 | 8.50 |

*Made by a method similar to that described in Example 12.

These paint formulations (U–Z) along with paint Q were tested by a method of Zabel and Horner for mildewcide activity as mentioned above. The results of this testing are given in Table 9, below. These results show that the paints containing the pyrithione biocide at extremely low levels is effective in controlling the growth of mildew on paint surfaces. Also, the pyrithione-containing paints exceed the performance of the commercial paint mildewcide TCIN even at 1/25 of the concentration of TCIN.

TABLE 9

Paint Mildewcide Test/Prototype and Commercial Paints

| Paint | % Biocide (Dry Weight) | Growth on Paint Surface 4 Weeks | 6 Weeks |
| --- | --- | --- | --- |
| U | 1.0 Pyrithione | 1 | 1 |
| V | 0.3 Pyrithione | 1 | 1 |
| W | 0.1 Pyrithione | 2 | 2 |
| X | 0.03 Pyrithione | 2 | 2 |
| Y | 0.01 Pyrithione | 2 | 2 |
| Z | None | 4 | 4 |

TABLE 9-continued

| Paint Mildewcide Test/Prototype and Commercial Paints | | | |
|---|---|---|---|
| | % Biocide | Growth on Paint Surface | |
| Paint | (Dry Weight) | 4 Weeks | 6 Weeks |
| Q | 0.25 TCIN | 3 | 3 |

Key for Table 9:
1 - No stain
2 - Lightly stained at bottom or a few light spots
3 - Heavily stained at bottom
4 - Uniformly stained

WOOD PRESERVATION TESTING

Wood preservatives are needed to prevent the rapid deterioration of wood products that are exposed to conditions which promote microbial growth and decay. Most wood preservatives are used to extend the useful life of exterior-exposed products by keeping the structural strength of the end-product from falling below usable levels. The ability to impart water-repellency is also considered important in marine applications. Current products suffer certain disadvantages such as environmental migration of the biocide and, toxicity when involving consumer contact. The present invention overcomes such migration problems by chemically bonding the desired bioactive agent to the polymer. This will also decrease any undesirable environmental effects.

This aspect of the present invention extends the utility of the above described antimicrobial polymers to the wood preservation area. Two general techniques are shown. In one, a solution of the polymer was applied to the wood directly. In the second, a solution of the corresponding monomers and a radical initiator was applied to the wood, followed by in-situ polymerization. Examples of both types of application with pyrithione methacrylate homopolymer and pyrithione methacrylate/methyl methacrylate copolymer are included. In examples of in-situ polymerization there exists the possibility of forming graft copolymers between the pyrithione-containing polymer and the polysaccharides structure of the wood. Evidence for the formation of the graft copolymer would be the inability to leach the polymer away from the wood employing organic solvents. This evidence was obtained. See Tables 10, Examples 32, 33, 37, 38, 41, C-4 and C-5.

EXAMPLE 29

Bulk In-Situ Copolymerization

Eight 1 1/16"×1 1/16"×¼" pine wood blocks weighing a total of 13.13 g were placed in a dish and a 5-6 mm Hg vacuum was applied for 30 min. A solution was prepared containing 6.0 g of pyrithione methacrylate (0.03 mole), 72.0 g of methyl methacrylate (0.72 mole), and 1.23 g of azobisisobutyronitrile (0.0075 mole). While still under vacuum the solution was added to the dish and the wood blocks were submerged in the monomer solution. After soaking for 30 minutes the wood blocks were removed from the monomer solution, excess monomer was wiped off and the blocks were heated at 75° C. for 16 hours. After cooling to room temperature the blocks weighed 25.49 g. The polymer was distributed throughout the wood chip.

EXAMPLE 30

Solution In-Situ Polymerization

Eight 1 1/16"×1 1/16"×¼" pine wood blocks weighing a total of 13.11 g were treated in the same manner as Example 29 except the monomer solution was a 1.50 g pyrithione methacrylate (0.0077 mole), 18.0 g methyl (0.18 mole) methacrylate, 0.31 g of AIBN (0.00185 mole), and 78 ml of toluene. The treated blocks weighed 15.28 g after polymerization.

EXAMPLE 31

Polymer Treated Wood Blocks

Four 1 1/16"×1 1/16"×¼" pine wood blocks weighing a total of 8.55 g were treated in the same manner as Example 29 except that a polymer solution prepared from 20 g of the polymer from example 10 dissolved in 80 ml of toluene was employed instead of the monomer solution. After the wood preservation treatment the wood blocks were allowed to air-dry for 48 hours. The treated blocks weighed 11.54 g.

EXAMPLE 32

Methylene Chloride Wash of Treated Wood Blocks

Four wood blocks weighing a total of 13.42 from Example 29 were placed in 300 ml of methylene chloride and stirred for 1 hour. The methylene chloride solution was removed and a fresh 300 ml of methylene chloride was added and stirring was continued. The solvent was replaced three times with fresh methylene chloride after an additional 1 hour, then after 2 more hours, and then another 2 more hours of stirring. The wood blocks were removed from the solvent and air-dried for 24 hours. The wood blocks then weighed 7.86 g.

EXAMPLE 33

Methylene Chloride Wash of Treated Wood Blocks

Four wood blocks weighing a total of 7.25 g from Example 30 were washed with methylene chloride by the same procedure as Example 32. The wood blocks then weighed 6.54 g after drying for 24 hours.

The procedures outlined above in Examples 32 and 33 solubilize and remove any polymer that was formed in the wood. The procedure should not remove any graft copolymers that formed during the polymerization. Thus, the increase in the total weight of the wood blocks over their original weight prior to any treatment is attributed to the formation of a graft copolymer between the pyrithione methacrylate and/or methyl methacrylate and the polysaccharides of the wood. These increases are shown in Table 10. Other similar results are shown in Examples 37, 38, 41, C-4 and C-5.

EXAMPLE 34

Bulk In-Situ Copolymerization

Eight 1 1/16"×1 1/16"×¼" pine wood blocks weighing a total of 16.22 g were treated in the same manner as Example 29 except the monomer solution was 1.5 g of pyrithione methacrylate (0.0077 mole), 94.4 g of methyl methacrylate (0.9429 mole). The treated blocks weighed a total of 31.86 g after polymerization.

EXAMPLE 35

Solution In-Situ Polymerization

Eight 1 1/16"×1 1/16"×¼" pine wood blocks weighing a total of 13.80 g were treated in the same manner as Example 29 except the monomer solution was 0.38 g of pyrithione methacrylate (0.00195 mole), 23.6 g of methyl methacrylate (0.236 mole), 0.39 g of AIBN (0.0023 mole) and 96 g of toluene. The treated blocks weighed 16.31 g after polymerization.

EXAMPLE 36

Polymer Treated Wood Blocks

Four 1 1/16"×1 1/16"×¼" pine wood blocks weighing a total of 8.37 g were treated in the same manner as Example 31 except that a polymer solution prepared from 20 g of the polymer from Example 9 dissolved in 80 ml toluene was exmployed instead of the monomer solution. After the wood preservation treatment the wood blocks were allowed to air-dry for 48 hours. The treated blocks weighed 11.54 g.

EXAMPLE 37

Methylene Chloride Wash of Treated Wood Blocks

Four wood blocks weighing a total of 15.83 g from Example 36 were washed with methylene chloride by the same procedure as Example 32. The wood blocks weighed a total of 9.26 g after drying for 24 hours.

EXAMPLE 38

Methylene Chloride Wash of Treated Wood Blocks

Four wood blocks weighing a total of 7.99 g from Example 35 were washed with methylene chloride by the same procedure as Example 32. The wood blocks weighed a total of 7.09 g after drying from 24 hours.

EXAMPLE 39

Solution In-Situ Homo-Polymerization

Eight 1 1/16"×1 1/16"×¼" pine wood blocks weighing a total of 13.55 g were treated in the same manner as Example 29 except the monomer solution was 18.0 g of pyrithione methacrylate (0.09 moles), 0.84 g of AIBN (0.005 moles), and 72 g of toluene. The treated blocks weighed a total of 17.63 g after polymerization. It should be noted that bulk polymerization is not amenable with making this homopolymer because pyrithione methacrylate is a solid.

EXAMPLE 40

Polymer Treated Wood Blocks

Four 1 1/16"×1 1/16"×¼— pine wood blocks weighing a total of 8.49 g were treated in the same manner as Example 31 except that a polymer solution prepared from 18 g of the polymer from Example 1B dissolved in 72 ml of toluene was employed instead of the monomer solution. After the wood preservation treatment the wood blocks were allowed to air-dry for 48 hours. The treated blocks weighed 9.63 g.

EXAMPLE 41

Methylene Chloride Wash of Treated Wood Blocks

Four wood blocks weighing 9.21 g from Example 41 were washed with methylene chloride by the same procedures as Example 34. The wood blocks weighed 7.03 g after drying.

COMPARISON 1

Bulk In-Situ Copolymerization

Eight 1 1/16"×1 1/16"×¼" pine wood blocks weighing 12.38 g were treated in the same manner as Example 31 except the monomer solution was 100.12 g of methyl methacrylate (0.2 moles) and 1.68 g of AIBN (0.01 moles). The treated blocks weighed a total of 24.70 g after polymerization.

COMPARISON 2

Solution In-Situ Polymerization

Eight 1 1/16"×1 1/16"×¼" pine wood blocks weighing a total of 14.23 g were treated in the same manner as Example 31 except the monomer solution was 20.02 g of methyl methacrylate (0.2 mole), 0.33 g of AIBN (0.002 moles), and 80 g of toluene. The treated blocks weighed 17.08 g after polymerization.

COMPARISON 3

Polymer Treated Wood Blocks

Four 1 1/16"×1 1/16"×¼" pine wood blocks weighing a total of 8.55 g were treated in the same manner as Example 31 except that a polymer solution prepared from 10 g of polymethyl methacrylate (Aldrich-low molecular weight), dissolved in 50 ml of toluene and 50 ml of methylene chloride was employed instead of the monomer solution. After the wood preservation treatment the blocks were allowed to air-dry for 48 hours. The treated blocks weighed 11.34 g.

COMPARISON 4

Methylene Chloride Wash of the Treated Wood Blocks

Four wood blocks weighing 13.34 g from Comparison 1 were washed with methylene chloride by the same procedure as Example 32. The wood blocks weighed 7.49 g after drying for 24 hours.

COMPARISON 5

Methylene Chloride Wash of the Treated Wood Blocks

Four wood blocks weighing a total of 8.91 g from Comparison 5 were washed with methylene chloride by the same procedure as Example 32. The wood blocks weighed 7.94 g after drying for 24 hours.

TABLE 10

| Example and Comparison No. | Polymer Type | Wt. % of Treated Wood Attributed to the Polymer |
|---|---|---|
| 29 | 5% Pyrithione methacrylate/ methyl methacrylate | 48.5 |
| 30 | 5% Pyrithione methacrylate/ methyl methacrylate | 14.0 |
| 31 | 5% Pyrithione methacrylate/ methyl methacrylate | 25.9 |
| 32 | 5% Pyrithione methacrylate/ methyl methacrylate | 4.4 |
| 33 | 5% Pyrithione methacrylate/ methyl methacrylate | 4.2 |
| 34 | 1% Pyrithione methacrylate/ methyl methacrylate | 49.1 |
| 35 | 1% Pyrithione methacrylate/ methyl methacrylate | 15.4 |
| 36 | 1% Pyrithione methacrylate/ methyl methacrylate | 27.5 |
| 37 | 1% Pyrithione methacrylate/ methyl methacrylate | 5.2 |
| 38 | 1% Pyrithione methacrylate/ methyl methacrylate | 2.3 |
| 39 | Pyrithione methacrylate | 23.1 |
| 40 | Pyrithione methacrylate | 11.8 |
| 41 | Pyrithione methacrylate | 0.6 |
| C-1 | Methyl methacrylate | 49.4 |
| C-2 | Methyl methacrylate | 15.9 |
| C-3 | Methyl methacrylate | 10.3 |
| C-4 | Methyl methacrylate | 5.3 |
| C-5 | Methyl methacrylate | 4.6 |

Commercial Wood Preservatives

The following commercial wood preservatives were employed for comparative testing. The wood preservatives were applied by the same method described in Example 31.

| Comparison No. | Wood Preservative | Biocide Present | Wt. of Treated Wood attributed to Preservative |
|---|---|---|---|
| C-6 | Weldwood, Woodlife[7] | 4.3% pentachlorophenols 0.5% other chlorophenols | 38.7 |
| C-7 | Evans, stain and wood preservative[8] | 0.4% Bis(tributyltin)oxide | 39.1 |

[7] Roberts Consolidated Industries, City of Industry, CA.
[8] Evans Products Company, Roanoke, VA.

Wood Rot Test

A test procedure was followed exactly from the following published procedure: H. P. Sutter, *International Biodeterioration Bulletin*, 14 (3), 95–99 (1978). The organisms employed were *Coniophora puteana* ATCC 36336 and *Lentinus lepideus* ATCC 12653 (a creosole-resistant fungus). Duplicates were run in each case. The growth of brown rot (cellulose-degrading) fungi on pine blocks after 25 days at 28° C. are evaluated as:

Growth Key for Table 11:
0—no growth
1—slight growth
2—moderate growth
3—heavy growth
4—very heavy growth These results in Table 11 show that pyrithione-containing polymers impregnated in wood, either through a pressure treatment or in-situ formation, were effective in controlling the growth of wood rot organisms while the methyl methacrylate polymer was not. After the methylene chloride washes, the remaining graft copolymers still gave complete control in the case of the homopolymer and moderate control in the other cases. The results also show pyrithione-containing polymers compare favorably against commercial wood preservatives tested in Comparisons C-6 and C-7.

TABLE 11

| Example or Comparison No. | Growth C. puteana | L. lepideus |
|---|---|---|
| untreated wood | 4,3 | 4,4 |
| 29 | 0,0 | 0,0 |
| 30 | 0,1 | 0,0 |
| 31 | 2,1 | 1,1 |
| 32 | 1,2 | 1,1 |
| 33 | 3,2 | 4,4 |
| 34 | 0,0 | 1,0 |
| 35 | 1,1 | 4,4 |
| 36 | 3,3 | 3,2 |
| 37 | 1,3 | 2,3 |
| 38 | 3,0 | 3,4 |
| 39 | 0,0 | 0,0 |
| 40 | 0,0 | 0,0 |
| 41 | 0,0 | 0,0 |
| C-1 | 2,1 | 4,4 |
| C-2 | 0,0 | 4,4 |
| C-3 | 1,1 | 4,4 |
| C-4 | 1,2 | 3,3 |
| C-5 | 4,3 | 4,3 |
| C-6 | 0,0 | 0,0 |
| C-7 | 1,1 | 3,1 |

Surface Treated Wood Blocks

Four 1 1./16"×1 1/16"×¼" pine wood blocks were surface treated with either a wood preservative comprising a 10% solution of a pyrithione methacrylate containing polymer in methylene chloride or a commercial wood preservative. The wood blocks were brush coated on all surfaces and in some cases multiple coats were applied. These examples were not pressure treated like the previous examples. These present examples correspond to what a consumer would do to apply a wood preservative.

The amount of biocide applied to each wood block was calculated by determining the weight increase of each wood block after treatment and calculating the biocide present in the weight increase. (See Table 12).

| Example | Weight % Biocide in Wood Preservative | Wood Preservative |
|---|---|---|
| 42 | 0.403% Pyrithione | Terpolymer from Example 13 |
| 43 | 0.730% Pyrithione | Terpolymer from Example 12 |
| 44 | 1.36% Pyrithione | Co-polymer from Example 11 |
| 45 | 1.36% Pyrithione | Co-polymer from Example 11 |
| 46 | 1.36% Pyrithione | Co-polymer from Example 11 |
| 47 | 1.36% Pyrithione | Co-polymer from Example 11 |
| C-8 | None | MMA/BA Co-polymer |
| C-9 | 4.3% Pentachlorophenol 0.5% Other Chlorophenols | Weldwood Woodlife |
| C-10 | 0.4% Bis(tributyltin)oxide | Evans stain and wood preservative |

The results from Table 12 show that pyrithione levels of 7 mg per wood block are effective in controlling *C. puteana*. Against *L. lepideus* 25 mg/wood block of pyrithione exhibited complete control and levels as low as 7 mg per wood block allow only slight fungal growth. In all cases pyrithione is superior to the negative control and compared favorably with commercial products.

TABLE 12

Wood Rot Test

| Example or Comparison No. | Average Weight Biocide (per Wood Block) | Growth C. puteana | L. lepideus |
|---|---|---|---|
| Untreated Wood | None | 4,4 | 4,4 |
| 42 | 7 mg pyrithion | 0,0 | 1,2 |
| 43 | 14 mg pyrithione | 0,0 | 1,1 |
| 44 | 10 mg pyrithione | 0,3 | 1,1 |
| 45 | 25 mg pyrithione | 0,0 | 0,1 |
| 46 | 41 mg pyrithione | 0,0 | 0,0 |
| 47 | 49 mg pyrithione | 0,0 | 0,0 |
| C-8 | None | 4,4 | 0,4 |
| C-9 | 43 mg penta chloro phenol 7 mg other chloro phenols | 0,0 | 0,0 |
| C-10 | 2 mg bis(tributyl tin) oxide | 0,0 | 2,2 |

Key:
0 No growth
1 Slight growth
2 Moderate growth
3 Heavy growth
4 Very heavy growth

Antimicrobial Testing

Several biofunctional polymers of Examples 1-16 were tested in a standard Minimum Inhibitory Concentration (MIC) test against 8 different bacteria and 8 different fungi. Also tested in this MIC test were poly methyl methacrylate, sodium pyrithione, DMSO and Triton X-200 as blanks. The results are given below in Tables 13 and 14.

The results show that the pyrithione containing polymers exhibit activity against a variety of bacteria and fungi. Both pyrithione methacrylate monomer and the pyrithione containing polymer have antimicrobial activity similar to sodium pyrithione on an equivalent weight basis of the pyrithione moiety present.

TABLE 13

Antimicrobial Testing - MIC in ppm

| | Sodium Pyrithione | Pyrithione Methacrylate | Poly Methyl Methacrylate | DMSO | Triton X-200 |
|---|---|---|---|---|---|
| Bacteria | | | | | |
| 1 | 256 | 256 | 1024 | 1024 | 1024 |
| 2 | 1024 | 1024 | 1024 | 1024 | 1024 |
| 3 | 256 | 256 | 1024 | 1024 | 1024 |
| 4 | 4 | 8 | 1024 | 1024 | 512 |
| 5 | 16 | 32 | 1024 | 1024 | 1024 |
| 6 | 32 | 64 | 1024 | 1024 | 1024 |
| 7 | 64 | 128 | 1024 | 1024 | 1024 |
| 8 | 2 | 0.5 | 512 | 1024 | 1024 |
| Fungi | | | | | |
| 1 | 0.5 | 1 | ND* | 1024 | 1024 |
| 2 | 0.25 | 0.25 | ND | 512 | 512 |
| 3 | 0.5 | 0.25 | ND | 1024 | 1024 |
| 4 | 0.25 | 0.25 | ND | 1024 | 1024 |
| 5 | 0.5 | 0.5 | ND | 1024 | 1024 |
| 6 | 0.25 | 0.25 | ND | 512 | 512 |
| 7 | 4 | 2 | ND | 1024 | 1024 |
| 8 | 2 | 8 | ND | 512 | 512 |

*ND = not determined

TABLE 14

Antimicrobial Testing of Pyrithione Containing Polymers MIC in ppm

| | Polymer (from Example) | | | | | |
|---|---|---|---|---|---|---|
| | 1B | 2 | 4 | 6 | 8 | 15 | 16 |
| Bacteria | | | | | | | |
| 1 | 1024 | 1024 | 1024 | 1024 | 1024 | 1024 | 1024 |
| 2 | 1024 | 1024 | 1024 | 1024 | 1024 | 1024 | 1024 |
| 3 | 1024 | 1024 | 1024 | 1024 | 1024 | 1024 | 1024 |
| 4 | 32 | 256 | 1024 | 128 | 1024 | 64 | 256 |
| 5 | 256 | 512 | 1024 | ND* | ND | 256 | 1024 |
| 6 | 256 | 1024 | 1024 | 256 | 1024 | 256 | 1025 |
| 7 | 256 | 1024 | 1024 | 512 | 1024 | 128 | 512 |
| 8 | 2 | 64 | 1024 | 512 | 1024 | 128 | 512 |
| Fungi | | | | | | | |
| 1 | 4 | 64 | 1024 | 64 | 1024 | 128 | 512 |
| 2 | 0.25 | 8 | 256 | 16 | 512 | 16 | 128 |
| 3 | 4 | 128 | 256 | 16 | 128 | 16 | 128 |
| 4 | 0.5 | 16 | 256 | ND | ND | 8 | 128 |
| 5 | 4 | 256 | 1024 | 16 | 1024 | 128 | 1024 |
| 6 | 0.25 | 0.25 | 32 | 2 | 64 | 2 | 32 |
| 7 | 4 | 64 | 512 | 32 | ND | 128 | 1024 |
| 8 | 16 | 128 | 512 | 0.5 | 512 | 256 | 512 |

*ND = not determined

| Key To Table 13 and 14 Microbiological Organisms | |
|---|---|
| Bacteria | |
| 1 | Pseudomonas aeruginosa ATCC 9027 |
| 2 | Pseudomonas aeruginosa (pyrithione resistant) |
| 3 | Enterobacter aerogenes ATCC 13048 |
| 4 | Staphylococcus aureus ATCC 6538 |
| 5 | Pseudomonas syringae ATCC 19310 |
| 6 | Pseudomonas phaseolicola ATCC 11355 |
| 7 | Xanthomonas vesicatoria ATCC 11551 |
| 8 | Xanthomonas phaseoli ATCC 19315 |
| Fungi | |
| 1 | Aspergillus niger ATCC 16404 |
| 2 | Trichophyton mentagrophytes ATCC 9533 |
| 3 | Candida albicans ATCC 10231 |
| 4 | Helminthosponium oryzae ATCC 34393 |
| 5 | Fuscarium oxysporum ATCC 15643 |
| 6 | Glomerella augulata ATCC 10593 |
| 7 | Aeternaria solani ATCC 11078 |
| 8 | Rhizoctonia solani ATCC 28268 |

Comparing Pyrithione-Containing Polymers to Their Monomers

EXAMPLE 48

A Trypticase Agar plate was swabbed with a suspension of *Aspergillus niger* ATCC 16404 spores. A well was punched out in the center of the plate with a #3 cork borer. Five milligrams of finely ground 1:24 pyrithione methacrylate/methyl methacrylate copolymer from Example 8 was added to the well and covered with 50 ul sterile distilled water. The plate was incubated at 28° C. for three days. There was no inhibition of growth of mold fibers on the plate and slight inhibition of sporulation at the edge of the well. This result shows that the polymer-bound pyrithione methacrylate does not leach readily from the polymer matrix.

COMPARISON 11

Five milligrams of pyrithione methacrylate monomer was tested as described in Example 1. A zone of inhibition of growth 45 mm in diameter and of inhibition of sporulation 54 mm in diameter was observed. This result shows that monomeric pyrithione methacrylate leaches easily in an aqueous environment.

EXAMPLE 49

The terpolymer of a emulsion polymerization of pyrithione methacrylate, methyl methacrylate and butyl acrylate, such as described in Example 16, is a milk-white latex suitable for direct formulation in a water-based paint of any desired color. Similarly, a solution of a pyrithione methacrylate/methyl methacrylate copolymer, such as that described in Example 8, in organic solvents such as toluene, methylene chloride, acetone, and the like is clear and nearly water-white. The copolymer is therefore suitable for direct incorportion in a solvent-based paint of any desired color.

COMPARISON 12

Both aqueous emulsions and organic solutions of pyrithione methacrylate monomer, even at concentrations of 0.1%, are bright, canary yellow. Therefore formulation of paints of colors other than yellow requires addition of excessive amounts of pigments to mask the yellow color, and, in cases where white, off-white, or pales hues are desired, may not be practical.

EXAMPLE 50

A sample of the pyrithione methacrylate/methyl methacrylate copolymer prepared as described in Example 8, was placed in a glass jar and stored at ambient conditions. After 24 months the copolymer showed no signs of degradation—it was free-flowing and retained its original color, demonstrating excellent storage stability.

COMPARISON 13

A sample of pyrithione methacrylate monomer, prepared as described in Example 1A, was placed in a glass jar and stored at ambient conditions. After about three days the yellow crystals had changed to a brown viscous oil, demonstrating the severe susceptibility of the monomer to thermal degradation.

What is claimed is:

1. A bioactive polymer comprising an effective biocidal amount of moieties derived from pyrithione and having the formula

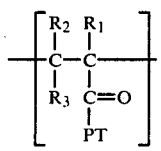

wherein $R_1$, $R_2$ and $R_3$ are individually selected from hydrogen and alkyl groups having from 1 to 4 carbon atoms; and PT represents the pyrithione moiety which is defined as

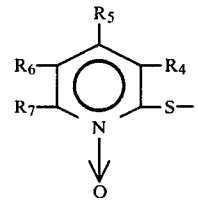

wherein $R_4$, $R_5$, $R_6$ and $R_7$ are individually selected from hydrogen and, a lower alkyl group having from 1 to about 8 carbon atoms, a lower alkoxy group having from 1 to about 8 carbon atoms, a nitro group and a halo group.

2. The bioactive polymer of claim 1 wherein $R_1=CH_3$ and $R_2$, $R_3$, $R_4$, $R_5$, $R_6$ and $R_7$ are all hydrogens.

3. The bioactive polymer of claim 1 wherein said polymer is a homopolymer.

4. The bioactive polymer of claim 3 wherein said polymer has an average molecular weight of about 1000 to about 1,000,000.

5. The bioactive polymer of claim 1 wherein said polymer is a copolymer comprising said moieties derived from pyrithione and moieties derived from at least one other ethylenically unsaturated comonomer.

6. The bioactive polymer of claim 5 wherein said polymer has an average molecular weight of about 1000 to about 1,000,000.

7. The bioactive polymer of claim 1 wherein said polymer is a graft copolymer with a polysaccharide.

8. The bioactive polymer of claim 7 wherein said polysaccharide is a cellulosic polysaccharide.

* * * * *

UNITED STATES PATENT AND TRADEMARK OFFICE
CERTIFICATE OF CORRECTION

PATENT NO. : 4,565,856

DATED : January 21, 1986

INVENTOR(S) : Trotz et al

It is certified that error appears in the above-identified patent and that said Letters Patent is hereby corrected as shown below:

In column 8, at line 35 after "was" and before "concentrated" delete the punctuation mark --,--.

In column 14, at line 37 delete "tested" and insert instead --diluted 1:3--.

In column 16, at lines 3 and 4 delete the column headings "Control Surface", "Treated Broth" and insert instead --Control Surface--, --Treated Surface-- and --Broth--.

In column 18, at line 22 after "the" and before "final" insert --polymer and this solvent was evaporated off during the--.

In column 23, at line 46 delete "1 1/16" x 1 1/16" x 1/4-" and insert instead --1 1/16" x 1 1/16" x 1/4"--.

Signed and Sealed this

Twenty-fifth Day of November, 1986

*Attest:*

DONALD J. QUIGG

*Attesting Officer*  *Commissioner of Patents and Trademarks*